United States Patent [19]

Blytas et al.

[11] Patent Number: 4,657,647
[45] Date of Patent: Apr. 14, 1987

[54] PROCESS FOR THE PRODUCTION OF DICHLOROHYDRIN AND THE ELECTRODIALYSIS THEREOF

[75] Inventors: George C. Blytas; F. Norman Grimsby, both of Houston, Tex.

[73] Assignee: Shell Oil Company, Houston, Tex.

[21] Appl. No.: 885,514

[22] Filed: Jul. 14, 1986

[51] Int. Cl.[4] .................. B01D 13/02; B01D 57/02
[52] U.S. Cl. ................................................ 204/182.4
[58] Field of Search ................................... 204/182.4

[56] References Cited

U.S. PATENT DOCUMENTS 3,909,382  9/1975  Mueller et al. .................. 204/182.4

FOREIGN PATENT DOCUMENTS 3129551  2/1983  Fed. Rep. of Germany ... 204/182.4
 105547  8/1975  Japan ................................ 204/182.4

Primary Examiner—Howard S. Williams
Attorney, Agent, or Firm—Ronald R. Reper

[57] ABSTRACT

A continuous process for the production of dichlorohydrin by the reaction of allyl chloride, water and chlorine enabling several options for improving yields, lowering operating costs and having reduced effluent treating requirements which multi-stage reaction zone process employs electrodialysis and post reaction reverse osmosis, with integrated recycled streams therebetween.

12 Claims, 1 Drawing Figure

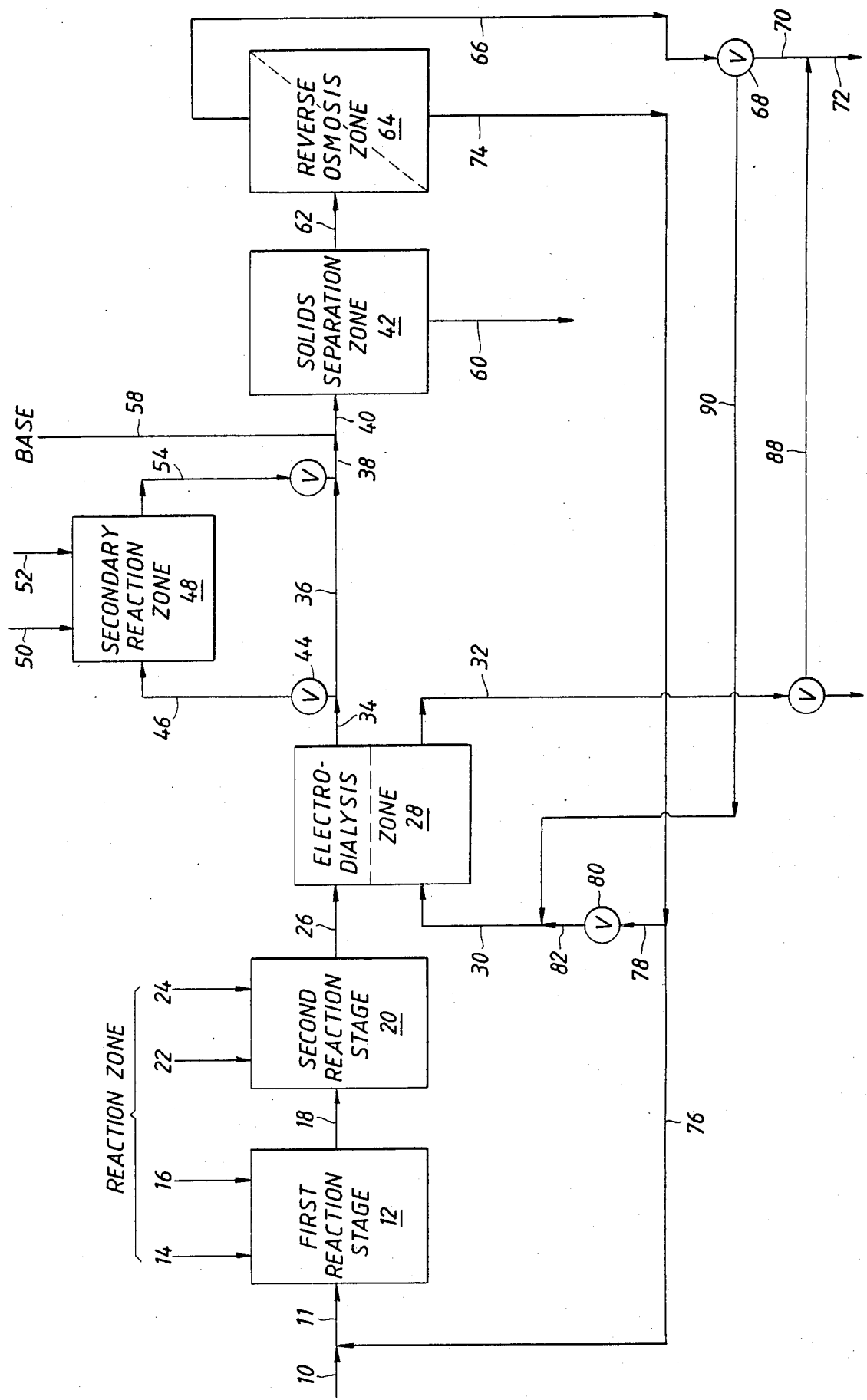

PROCESS FOR THE PRODUCTION OF DICHLOROHYDRIN AND THE ELECTRODIALYSIS THEREOF

BACKGROUND OF THE INVENTION

It is known to prepare an aqueous solution of dichlorohydrins e.g., 2,3 dichloro-1-propanol and 1,3 dichloro-1-propanol, herein collectively dichlorohydrin, by reacting in a reaction zone allyl chloride, water and chlorine in dilute aqueous phase.

U.S. Pat. No. 2,714,121, incorporated herein by reference, discloses producing halohydrins by using high dilution of e.g., 250 to 400 volumes of water per volume of e.g., a halosubstituted hydrocarbon in aqueous medium with subsequent addition of the halogen, and keeping the organic by-product phase dispersed as fine particles.

U.S. Pat. No. 2,714,123, incorporated herein by reference, discloses producing an aqueous solution of dichlorohydrin in a series of reaction zones wherein substantially all of the water is fed to the first of the reaction zones and the other reactants are added in substantially equimolar proportions into each of the other reaction zones.

U.S. Pat. No. No. 3,909,382 discloses recovering acid values, such as hydrochloric acid formed during olefin chlorohydrination, by series flow through a plurality of electrodialysis states to upgrade the acid to higher concentration.

From Japanese Patent 74,000369 it is known that the product mixture from the reaction of a lower olefin, chlorine and water can be electrodialyzed to remove the by-product ions of hydrogen and chlorine, and the ion-depleted chlorohydrin solution circulated to the single reaction zone, enabling the production of a concentrated aqueous chlorohydrin solution.

A disadvantage of the known processes is that substantial amounts of water are used in the reaction zone of the process to obtain higher selectivity, that is the yield of the desired chlorohydrin product, based upon the chemical feed. Such conventional processes result in a substantial volume of aqueous effluent containing minor amounts e.g., 1000 to 2000 parts per million by weight (ppmw) of organic impurities. Such effluent requires energy intensive treatment to reduce the amount of organic materials to low levels acceptable to be passed to receiving bodies of water such as rivers, lakes and the like. The present invention provides a method for both improving selectivity to the desired dichlorohydrin product and enabling reduction in the amount of aqueous effluent, thereby effecting great energy savings for the overall process.

SUMMARY OF THE INVENTION

According to the invention, there is provided a continuous process for the production of dichlorohydrin which comprises in sequence (a) reacting allyl chloride, water and chlorine in a reaction zone to form an aqueous reaction mixture of dichlorohydrin and reaction by-products, (b) passing said reaction mixture as feed to an electrodialysis zone, said electrodialysis zone having a feed inlet and a diluate (product) outlet, a concentrate inlet and a concentrate outlet, (c) electrodialyzing said feed in said electrodialysis zone to remove ions from said feed into a concentrate stream and to obtain a diluate stream containing dichlorohydrin and having a lower ion content then said feed, (d) adding a basic material to said dilute stream to neutralize at least a majority of the hydrogen ions present in said diluate while maintaining the pH of said diluate below about 6.9, (e) subjecting said diluate to reverse osmosis in a reverse osmosis zone to obtain: (1) retentate stream having a higher dichlorohydrin concentration than said diluate, and (2) a permeate stream of relatively pure water, (f) recycling a major portion of said permeate stream to the reaction zone, (g) passing a portion of at least one of: (1) said permeate stream and/or (2) said retentate stream, to the concentrate inlet of said electrodialysis zone, (h) withdrawing an ion concentrate stream from said electrodialysis zone, and (i) withdrawing any retentate stream which was not passed to said electrodialysis zone.

THE DRAWING

The FIGURE depicts a schematic flow diagram of a preferred embodiment of the invention.

DESCRIPTION OF PREFERRED EMBODIMENTS

In the principal reaction, allyl chloride is converted to a mixture of the two isomers of glycerol dichlorohydrin by reaction with hypochlorous acid, HClO, which is readily formed when chlorine is dissolved in water. The dichlorohydrination reaction takes place readily at temperatures in the range from about 15° to about 55° C.

As described in U.S. Pat. No. 2,714,121 the reaction may be carried out at a high water dilution in a reaction zone comprising a stirred reaction vessel or a loop reactor; preferably the reaction zone comprises a plurality of reaction stages arranged in series flow. The reaction mixture typically has a low pH value resulting from the hydrogen chloride formed as by-product in the series of chemical reactions. For maximum dichlorohydrin yield it is necessary to operate at low concentration of both chloride ion and of dichlorohydrin, i.e., with high water dilution which reduces the formation of undesired by-products such as, e.g., trichloropropane and tetrachloropropyl ether.

It is an advantage of the present invention that it provides great flexibility in the ability to control operating parameters so as to enable improved selectivity to the desired dichlorohydrin product, and reduced operating expense and/or increased throughout compared to conventional process designs. It is a further advantage that the integrated use of membrane steps according to the invention may be readily adapted i.e., retrofitted, into existing multi-stage series flow dichlorohydrin production facilities. It is an advantage of the present invention that by use of the combination of electrodialysis and reverse osmosis that significantly smaller reverse osmosis membrane area and/or reduced pressure is required, i.e., lower plant costs are achieved compared to the use of either membrane process step alone.

According to the invention the reaction zone may comprise from two to six reaction stages arranged in series flow. More than six reaction stages can be used, if desired. A particularly preferred mode of operation is to feed substantially all the water to the first of the reaction stages and add the other reactants in substantially equimolar proportions to the first stage and to each of the subsequent stages, as disclosed in U.S. Pat. No. 2,714,123.

In the process of the invention the reaction mixture effluent from the reaction zone is fed to an electrodialysis zone having a feed inlet and a product (diluate) outlet, a concentrate inlet and a concentrate outlet. The reaction mixture effluent is electrodialyzed in the electrodialysis zone to afford: (1) an electrodialysis concentrate stream having an inorganic chloride content greater than said feed, and (2) a diluate stream containing organic chloride compounds, particularly dichlorohydrin, and having a lower inorganic chloride content than said feed. The diluate stream is passed as feed to a reverse osmosis zone, or in a preferred embodiment to a secondary reaction zone. The concentrate stream is withdrawn for further processing as will be hereinafter described.

Electrodialysis is by now a well established industrial process. Basically, an electrodialysis unit comprises a plurality of membranes alternately anionic and cationic placed between an anode and a cathode connected to a direct current source. The membranes are usually separated from each other by 1 to 5 mm using appropriate spacers and the feed stream may be made to flow through a spacer creating a tortuous path in order to increase turbulence of the liquids contacting the membranes or insheet-type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exchange membranes).

If a feed stream is introduced uniformly from the top of the electrodialysis unit, it will be found that passages in the unit having an anion membrane on the cathode side of the passage and vice versa will become concentrate streams richer in ionized (herein saline) components and the other streams in passages bounded by anion membranes on the anoide side and cathode membranes on the cathode side will become depleted in ionized components. Such depleted stream or streams are herein referred to as the diluate stream.

When a direct current is applied across the two electrodes (anode and cathode) anions will tend to migrate towards the anode passing through the anion exchange membrane and being stopped by the first cation exchange membrane. In like manner, cations will cross through the cationic exchange membrane and will be stopped by the anionic exchange membranes. However, non-electrolyte species are not prevented from passing through the exchange membranes, except in so far as these are made of a tighter pore structure, even so, however, non-electrolytes will migrate through the membranes, the actual amount of migration depending on relative volume of diluate/concentrate streams.

The anionic and cationic membranes employed herein are known in the art. Generally, the anionic and cationic membranes comprise flat sheets of inorganic or organic materials which have extreme water-insolubility. Preferably the anionic and cationic membranes are prepared from synthetic organics resinous, polymeric materials, (e.g., polystyrene polymers) to which are bonded ionic groups. Any strong or weak base (e.g., tertiary amines or quaternary ammonium compounds) can be chemically bonded to the organic material to form cationic membranes; any strong or weak acid (e.g., aryl sulfonates) can be chemically bonded to the organic resinous material to form anionic membranes.

Generally, the anionic and cationic membranes herein, either in the form of laminate or a homogeneous cast or sheet, are "backed" or reinforced with an imbedded screen or matrix of synthetic reinforcing fabric, for example, Dynel, a vinylidene copolymer, or fiberglass to provide them with a substantially rigid structure. Other 'backings' can be used, provided the anionic and cationic membranes remain essentially impervious to mass flow but porous enough to permit ion megration or transfer.

The cation and anion-exchange membranes can be any cationand anion-selective membranes respectively which are essentially stable in the feed water and not chemically degraded by the components therein. Exemplary membranes are disclosed in the article entitled "Electrodialysis", Kirk-Othmer, Encyclopedia of Science and Technology, pages 846-865 (Second Edition, Interscience Publishers, 1965) and U.S. Pat. Nos. 2,730,768, 2,762,272, 2,860,097 and 3,616,385 incorporated herein by reference.

If desired, additional electrodialysis zones may be installed intermediate to stages in the reaction zone; however, these add to expense of the plant and, owing to the generally lower chloride content in the reaction mixture product from the upstream reaction stages, will generally consume more power per unit of chloride ion removed.

In a preferred embodiment, the diluate stream is passed to a secondary reaction zone wherein allyl chloride and chlorine are added in substantially equimolar amounts to form additional dichlorohydrin product, and additional hydrogen chloride by-product. However, the low amount of chloride present permits a higher selectivity to the dichlorohydrin than would be possible if the stoichiometric amount of chloride was present in the reaction mixture.

The dichlorohydrin-containing diluate, or when a secondary reaction zone is used, the effluent from secondary reaction zone is reacted with a basic substance to neutralize at least a major amount of the hydrogen ions present in said diluate, or said effluent, however, while not permitting the pH to exceed about 6.9. The use of excess basic substance is to be avoided to preclude conversion of the dichlorohydrin to epichlorohydrin and further undesirable side reactions such as hydrolysis and hydration of the epichlorohydrin. Although in theory any basic substance can be employed, preference is given to the hydroxides and carbonates of the alkali metals and/or alkaline earth metals. Particularly preferred because of their availability and generally lower cost are caustic soda (sodium hydroxide), lime (calcium hydroxide), and limestone (calcium carbonate).

Optionally, after the neutralization step the dichlorohydrin-containing diluate stream or secondary reaction zone effluent stream may be subjected to a solids removal step to remove any undissolved materials from said streams so as to minimize fouling of the membranes in the subsequent processing steps. When there are substantial amounts of solids present, e.g., when a lime slurry is employed as the basic substance, the solids removal step may comprise any known technique such as sedimentation, centrifugation or filtration. Microporous ultrafiltration is preferred. Any separated solids may be removed from the process, or if desired may be recycled to the base addition step of the present process.

The dichlorohydrin content of said dichlorohydrin-containing stream is then concentrated by reverse osmosis i.e., by applying hydraulic pressure against said stream and a suitable membrane, said pressure being greater than the osmotic pressure of said stream. The dichlorohydrin-containing stream is fed to a reverse osmosis zone and subjected to reverse osmosis to obtain: (1) a retentate stream having a higher dichlorohydrin concentration than said feed, and (2) a permeate stream of relatively pure water.

The reverse osmosis membranes used in the reverse osmosis zone may require some care in selection, since they are required to retain substantially all of the organics in the retentate stream. A conventional polysulfone membrane has been found useful for this purpose, as have thin film composite membranes.

At least a major portion of said permeate stream is recycled to the reaction zone. This recycled permeate stream can be used to displace the fresh water normally fed to the reaction zone, or, if desired, be supplied as additional water to further dilute the reactants in each reaction stage, thereby enabling greater selectivity to the desired dichlorohydrin product. The permeate stream may be divided to flow to each individual stage within the reaction zone, but preferably substantially all of the permeate is passed to a single reaction stage, and most preferably to the first reaction stage.

If desired, a minor portion of the permeate stream may be passed as feed to the concentrate inlet of the electrodialysis zone so as to reduce the ion concentration gradient across the electrodialysis membranes, thereby enabling higher efficiency in the electrodialysis step. In the process of the invention the reaction mixture product is fed to an electrodialysis zone having a feed inlet and a product (diluate) outlet, a concentrate inlet and a concentrate outlet. The reaction mixture is fed to and is electrodialyzed in the electrodialysis zone to afford: (1) an electrodialysis concentrate stream having an inorganic chloride content greater than said feed, and (2) a diluate stream containing organic chloride compounds, particularly dichlorohydrin, and having a lower inorganic chloride content then said feed. The diluate stream may, if desired, be passed as feed to a secondary reaction zone. The concentrate stream is withdrawn for further processing as will be hereinafter described.

The retentate stream may be withdrawn from the reverse osmosis zone for recovery of the dichlorohydrin by e.g., solvent extraction, or for conversion into derivatives such as epichlorohydrin and/or glycerine. Alternatively, part or substantially all of the retentate stream is passed to the concentrate inlet of the electrodialysis zone as the ion receiving stream for the electrodialysis step. In this manner any dichlorohydrin which permeates the electrodialysis membrane is readily recovered, and more importantly the electrodialysis step is rendered more efficient by reducing the ion-gradient across the electrodialysis membrane, and the total volume of the dichlorohydrin-containing stream need not be increased to achieve this efficiency.

When only a small amount of the permeate stream is passed to the concentrate inlet of the electrodialysis zone to receive the ions, the saline concentrate stream from said zone will ordinarily have only low organic content and may be withdrawn for further processing and/or disposal. When part or substantially all of the osmotic concentrate stream is passed to the concentrate inlet of the electrodialysis zone the concentrate outlet stream from said zone may be combined with any of the retentate stream not passed to said concentrate inlet, for further processing. Alternatively, when only part of the retentate stream is passed to the concentrate inlet of the electrodialysis zone, the more saline product existing the concentrate outlet of said zone need not be combined with any osmotic concentrate stream which was not passed to said electrodialysis zone but may be withdrawn for separate and/or different further processing.

The choice of whether to circulate some of the permeate and/or some or substantially all of the retentate stream to the concentrate inlet of the electrodialysis zone will depend upon local factors at the process location, such as e.g., the cost of electrical power, waste treating capabilities, water availability and raw material costs. The process according to the invention provides the flexibility to adapt operating parameters to changing conditions.

An embodiment of the invention will be described with reference to the figure which shows diagrammatically a preferred assemblage according to the invention. In the figure a fresh water stream is continuously introduced through conduits 10 and 11 at a rate of about 800 gpm and about 1300 gpm of recycle water through conduits 74, 76 and 11 into first reaction stage 12 of the reaction zone. Allyl chloride is continuously fed into said first reaction stage through conduit 14, while chlorine in an amount substantially equimolar with respect to the allyl chloride is fed via conduit 16. The reaction mixture is circulated at a high rate and at a temperature of about 55° C. in said first stage. Effluent from said first stage comprising about 0.11M dichlorohydrin and about 0.1N HCl is passed via conduit 18 to second reaction stage 20. As with the previous reaction stage, allyl chloride is continuously fed through conduit 22 into the rapidly circulated reaction mixture in the second stage, and a substantially equimolar amount of chlorine is fed through conduit 24. The reactions in each stage are mildly exothermic.

A portion of the second stage reaction mixture is continuously diverted to an electrodialysis zone 28. The second stage reaction effluent containing about 0.16 M dichlorohydrin and about 0.15 N HCl is continuously fed through conduit 26 to said electrodialysis zone, which may comprise one or more conventional electrodialysis units in parallel flow to achieve the membrane area required for the desired flow and amount of ion separation. Electrodialysis zone 28 is comprised of alternating anionic exchange membranes designated as 203 QZL-386 and cationic membranes designated as 61 CZL-386, which membranes are available from Ionics, Inc., Watertown, Massachusetts. In general the voltage across each stack of membranes is arranged so that there is a voltage of about 0.5 to about 3.0 volts per cell pair, with a voltage in the range from about 1.0 to about 2.5 being preferred. The ions are removed into a concentrate stream which enters the electrodialysis zone via conduit 30 and exits via conduit 32. From electrodialysis zone 28 a diluate stream comprising about 0.17 M dichlorohydrin and about 0.05 N HCl is continuously passed via conduit 34, valve 44 and conduit 46 to secondary reaction zone 48, which may comprise one or more reaction stages in series flow. To the diluate fed into secondary reaction zone 48, additional allyl chloride is added via conduit 50 and additional chlorine in substantially equimolar amount via conduit 52. The reaction effluent from the secondary reaction zone 48, containing about 0.22 dichlorohydrin and about 0.1 N HCl is passed via conduit 52, valve 56 and conduits 38 and 40 to solids separation zone 42, which may be e.g., a filter press, deep bed filtration unit or a sedimentation clarifier unit. Preferably it is an ultrafiltration unit with e.g., a polysulfone membrane. Good results have been achieved with a membrane having a nominal flux of 150 GFD at 50 psi in distilled water. To the reactive effluent in conduit 38 a base, such as calcium hydroxide, is added via conduit 58 to neutralize at least a majority of the hydrogen ions present in said reaction effluent while maintaining the pH of said effluent below about 6.9 and, preferably below about 6.6. Any solids separated from said reaction effluent in solids-separation zone 42, are withdrawn via conduit 50. The solids-free reaction effluent is pumped (pump not shown) via conduit 52 to reverse osmosis zone 54. It is an advantage of the present invention that by use of the combination of electrodialysis and reverse osmosis that significantly smaller reverse osmosis membrane area and/or reduced pressure is required, i.e. lower plant costs are achieved compared to the use of either membrane process step alone.

Reverse osmosis zone 64 contains a thin film composite membrane. The solids-free reaction effluent is fed at a rate of about 2000 gpm to said zone at a pressure of about 850 psi resulting in (1) a retentate stream of about 600 gpm containing about 0.58 N dichlorohydrin, about 1400 gpm of a permeate stream of relatively pure water containing only about 0.01 M dichlorohydrin. The retentate is passed via conduit 66, valve 68, and conduits 70 and 72 and is withdrawn for separate and/or further processing, such as conversion into derivatives such as epichlorohydrin and/or glycerine. A major amount, e.g., about 1300 gpm, of the permeate stream is recycled via conduits 74, 76 and 11 to the first reaction stage 12. A small portion of said permeate stream e.g., about 100 gpm is diverted via conduits 74 and 78, valve 80 and conduits 82 and 30 to the concentrate inlet of electrodialysis zone 28 to act as an ion receiving stream, thereby reducing the ion concentration gradient across the electrodialysis membranes. From the electrodialysis zone the ion-laden concentrate stream exists via conduit 32 and may be withdrawn via valve 84 and conduit 86 for further treatment and/or disposal. Alternatively, said concentrate stream may be passed via conduit 32 valve 84 and conduit 88 to be combined with the retentate stream in conduit 72, in order to recover the small amount of dichlorohydrin which may have permeated the membranes in elecrtrodialysis zone 28.

In an alternate embodiment, from reverse osmosis zone 64 all e.g., about 1400 gpm of the premeate stream is passed via conduits 74, 76 and 11 to the first reaction stage 12, and all e.g., about 600 gpm or only part of the retentate stream is diverted via conduit 66 valve 68, and conduits 90 and 30 to electrodialysis zone 28 to act as the ion receiving stream. When only part of the retentate stream is diverted to the electrodialysis zone, the concentrate stream which exits via conduit 32 may be passed via valve 84 and conduit 86 for separate processing, e.g., into one derivative, and the remaining part of the retentate stream withdrawn via conduits 66 valve 68 conduits 70 and 72 for processing into another derivative. If desired, the part of the retentate stream which has passed through the electrodialysis zone to become the concentrate stream may be passed via conduit 32 valve 84 and conduits 88 and 72 to be combined with the retentate stream which has not passed through the electrodialysis zone 28.

What is claimed is:

1. A continuous process for the production of dichlorohydrin which comprises in sequence
    (a) reacting allyl chloride, water and chlorine in a first reaction to form an aqueous reaction mixture of dichlorohydrin and reaction by-products,
    (b) passing the reaction mixture as feed to an electrodialysis zone, said electrodialysis zone having a feed inlet and a diluate (product) outlet, a concentrate inlet and a concentrate outlet,
    (c) electrodialyzing said feed in said electrodialysis zone to remove ions formed during the reaction from said feed into a concentrate stream and to obtain a diluate stream containing dichlorohydrin and having a lower ion content than said feed,
    (d) adding a basic material to said diluate stream to neutralize at least a majority of the hydrogen ions present in said diluate while maintaining the pH of said diluate below about 6.9,
    (e) subjecting said diluate to reverse osmosis in a reverse osmosis zone to obtain: (1) an retentate stream having a higher dichlorohydrin concentration than said diluate, and (2) a permeate stream of relatively pure water,
    (f) recycling a major portion of said permeate stream to the reaction zone,
    (g) passing at least a portion of at least one of: (1) said permeate stream and/or (2) said retentate stream, to the concentrate inlet of said electrodialysis zone,
    (h) withdrawing an ion concentrate stream from said electrodialysis zone, and
    (i) withdrawing any retentate stream which was not passed to said electrodialysis zone.

2. A process as in claim 1 wherein said reaction zone comprises from 2 to 6 reaction stages.

3. A process as in claim 1 wherein substantially all of the permeate from the reverse osmosis zone is passed to said reaction zone.

4. A process as in claim 3 wherein substantially all of said permeate is passed to the first stage of said reaction zone.

5. A process as in claim 1 wherein substantially all of said retentate stream is passed to the concentrate inlet of the electrodialysis zone.

6. A process as in claim 1 wherein intermediate to steps (d) and (e), said reaction mixture is subjected to a solids-separation step to separate any insoluble material and afford a liquid depleted in insoluble material, and said liquid is passed as feed to the reverse osmosis zone of step (e).

7. A process as in claim 1 wherein the ion concentrate stream from step (h) and the retentate stream from step (i) are combined for further processing.

8. A continuous process for the production of dichlorohydrin which comprises in sequence
    (a) reacting allyl chloride, water and chlorine in a first reacion zone to form an aqueous reaction mixture of dichlorohydrin and reaction by-products,
    (b) passing said reaction mixture as feed to an electrodialysis zone, said electrodialysis zone having a feed inlet and a diluate (product) outlet, a concentrate inlet and a concentrate outlet,
    (c) electrodialyzing said feed in said electrodialysis zone to remove ions formed during the reaction from said feed into a concentrate stream and to obtain a diluate stream containing dichlorohydrin and having a lower ion content than said feed, (d) passing said diluate stream to a secondary reaction zone wherein additional allyl chloride and chlorine are added in substantially equimolar amount to form additional dichlorohydrin, and withdrawing a secondary reaction zone effluent having a higher dichlorohydrin content than said diluate stream, (e) adding a basic substance to said secondary reaction zone effluent to neutralize at least a majority of the hydrogen ions present while maintaining the pH of said effluent below about 6.9, (f) subjecting the product of step (e) to reverse osmosis in a reverse osmosis zone to obtain: (1) retentate stream having a higher dichlorohydrin concentration than said diluate, (2) a permeate stream of relatively pure water, (g) recycling a major portion of said permeate stream to the reaction zone, (h) passing at least a portion of at least one of: (1) said permeate stream and/or (2) said retentate stream, to the concentrate inlet of said electrodialysis zone, (i) withdrawing an ion concentrate stream from said electrodialysis zone, and (j) withdrawing any retentate stream which was not passed to said electrodialysis zone.

9. A process as in claim 8 wherein substantially all of said permeate is passed to the first stage of said reaction zone.

10. A process as in claim 8 wherein substantially all of said retentate stream is passed to the concentrate inlet of said electrodialysis zone.

11. A process as in claim 8 wherein intermediate to steps (e) and (f), said reaction mixture is subjected to a solids-separation step to separate any insoluble material and afford a liquid depleted in insoluble material, and said liquid is passed as feed to the reverse osmosis zone of step (f).

12. A process as in claim 8 wherein the ion concentrate stream from step (i) and the retentate stream from step (j) are combined for further processing.

* * * * *